US00RE44873E

(19) United States
(12) Reissued Patent
Guo et al.

(10) Patent Number: US RE44,873 E
(45) Date of Reissued Patent: Apr. 29, 2014

(54) IMIDAZOLE-5-CARBOXYLIC ACID DERIVATIVES, THE PREPARATION METHOD THEREFOR AND THE USES THEREOF

(71) Applicant: Salubris Asset Management Co., Ltd., Shenzhen, Gaungdong (CN)

(72) Inventors: Jianhui Guo, North Potomac, MD (US); Dong An, Shanghai (CN)

(73) Assignee: Salubris Asset Management Co., Ltd., Shenzhen, Guangdong (CN)

(21) Appl. No.: 13/727,587

(22) Filed: Dec. 26, 2012

Related U.S. Patent Documents

Reissue of:
(64) Patent No.: 7,858,651
Issued: Dec. 28, 2010
Appl. No.: 11/576,094
PCT Filed: Jul. 31, 2006
PCT No.: PCT/CN2006/001914
§ 371 (c)(1),
(2), (4) Date: Mar. 27, 2007
PCT Pub. No.: WO2007/095789
PCT Pub. Date: Aug. 30, 2007

(30) Foreign Application Priority Data

Feb. 20, 2006 (CN) ..... 2006 1 0023991

(51) Int. Cl.
*A61K 31/41* (2006.01)
*C07D 257/04* (2006.01)

(52) U.S. Cl.
USPC ..... 514/381; 548/253

(58) Field of Classification Search
None
See application file for complete search history.

(56) References Cited

U.S. PATENT DOCUMENTS

| | | | |
|---|---|---|---|
| 5,138,069 | A | 8/1992 | Carini et al. |
| 5,196,444 | A | 3/1993 | Naka et al. |
| 5,298,519 | A | 3/1994 | Binder et al. |
| 5,616,599 | A | 4/1997 | Yanagisawa et al. |
| 7,858,651 | B2 | 12/2010 | Guo et al. |
| 7,943,648 | B2 | 5/2011 | Guo et al. |
| 8,138,214 | B2 | 3/2012 | Lu et al. |
| 8,178,569 | B2 | 5/2012 | Guo et al. |
| 2009/0036505 | A1 | 2/2009 | Guo et al. |
| 2009/0326024 | A1 | 12/2009 | Guo et al. |
| 2009/0326025 | A1 | 12/2009 | Lu et al. |
| 2010/0168193 | A1 | 7/2010 | Guo et al. |
| 2010/0292286 | A1 | 11/2010 | Guo et al. |

FOREIGN PATENT DOCUMENTS

| | | | |
|---|---|---|---|
| CN | 1071426 | | 4/1993 |
| CN | 101024643 | | 8/2007 |
| EP | 0535420 | A1 | 4/1993 |
| EP | 0253310 | | 1/1998 |
| EP | 1988090 | A1 | 11/2008 |
| EP | 2103610 | | 9/2009 |
| EP | 2116242 | A1 | 11/2009 |
| WO | WO 2005/011646 | | 2/2005 |
| WO | WO 2005/011646 | A2 | 2/2005 |
| WO | WO 2005/023182 | | 3/2005 |
| WO | WO 2005/023182 | A2 | 3/2005 |
| WO | WO 2006/115187 | | 11/2006 |
| WO | WO 2007/095789 | A1 | 8/2007 |
| WO | WO 2008/067687 | A1 | 6/2008 |

OTHER PUBLICATIONS

Aug. 1, 2011 USPTO Notice "Clarification of Criteria for Reissue Error in View of In re Tanaka".
Notice of Allowance dated Jul. 9, 2012, U.S. Application No. 12/663,183.
International Search Report of PCT/CN2006/003301, dated Jun. 28, 2007.
International Search Report issued in PCT/CN2008/000048, dated Apr. 17, 2008.
Mealy et al., "Elisartan Potassium. Antihypertensive Angiotensin II Antagonist," Drugs of the Future. vol. 21, No. 2, 1996, pp. 139-142.
Wolf, S., et al., Sind alle Antihypertensiva nephroprotektiv? (2004), Herz 29, Nr. 3, pp. 248-254.
Naylor et al., "Potent imidazole angiotensin II antagonists: acyl sulfonamides and acyl sulfamides as tetrazole replacements," Bioorganic & Medicinal Chemistry Letters, vol. 4, No. 1, P69-74, (1994).
Dahlof, B., End-Organ Damage: does it really matter how we prevent it? (2003), European Heart Journal Supplements 5 (Supplement F), pp. F33-F39.
Grandi A.M., et al., Blockade of the renin-angiotensin-aldosterone system: effects on hypertensive target organ damage (2006), vol. 4, Cardiovascular and Hematological Agents in Medicinal Chemistry, pp. 219-228.
Ma, et al., "Effects of Losartan on Cardiac and Renal Functions in Elderly Hypertensive Patients", Journal of Jilin University (Medicine Edition), vol. 31, 2005, pp. 620-622.
Harwood et al. "Experimental Organic Chemistry, Standard and Microscale", Blackwell Science Ltd. p. 131 (1999).
Supplementary European Search Report corresponding to European Application No. 08038798 dated Nov. 30, 2010.
International Search Report and Written Opinion for corresponding PCT application No. PCT/CN2008/001715, date of mailing Jan. 22, 2009.
Byrn et al. Solid-State Chemistry of Drugs, 2d, Chapter 11 Hydrates and Solvates, 233-247 (1999).*
Morisette et al. Adv. Drug Delivery Rev. 56, 275-300 (2004).*
A.M. Rouhi, Chem. & Eng. News, Feb. 24, 2003, 81(8), 32-35.*
Drugs of the Future, 1996, vol. 21, No. 2, P139-142, Mealy, N. 35 al., "Elisartan Potassium. Antihypertensive angiotensin II antagonist, HN-6502 1".
Bioorganic & Medicinal Chemistry Letters, vol. 4, No. 1, P69-74, Elizabeth M. Naylor et al., "Potent Imidazole Angiotension II Antagonists: Acyl Sulfonamides and Acyl Sulfinamides as Tetrazole Replacements", (1994).

* cited by examiner

*Primary Examiner* — Michael Barker
(74) *Attorney, Agent, or Firm* — Finnegan, Henderson, Farabow, Garrett & Donner LLP

(57) ABSTRACT

The invention discloses imidazole-5-carboxylic acid derivatives, and their preparation methods. The derivatives of the invention are Angiotensin II receptor antagonists with angiotensin II antagonistic activity and antihypertensive activity, and thereby can be used as a therapeutical agent to treat hypertension.

17 Claims, No Drawings

IMIDAZOLE-5-CARBOXYLIC ACID DERIVATIVES, THE PREPARATION METHOD THEREFOR AND THE USES THEREOF

Matter enclosed in heavy brackets [ ] appears in the original patent but forms no part of this reissue specification; matter printed in italics indicates the additions made by reissue.

CROSS-REFERENCE TO RELATED APPLICATION

This Application *is a reissue application of U.S. Pat. No. 7,858,651, which* is a Section 371 National Stage Application of International Application No. PCT/CN2006/001914, filed 31 Jul. 2006 and published as WO 2007/095789 A1 on Aug. 30, 2007, the subject matter of which [are] *is* hereby incorporated by reference in its entirety*, which claims the benefit of priority of Application No. 2006 1 0023991, filed on Feb. 20, 2006, in China*.

TECHNICAL FIELD

The invention relates to imidazole-5-carboxylic acid derivatives, their preparation methods and their use as antihypertensive drugs.

BACKGROUND OF THE INVENTION

Angiotensin II, a main vasoconstrictor hormone of renin-angiotension-aldosterone system (RAAS), plays an important role in pathological physiology of many chronic diseases. The production approach of Angiotensin II which is present in various tissues is mainly as follows: angiotensinogen acted on by renin can be converted to angiotensins I (Ang I) of decapeptide which only has little activity in contraction of blood vessel; and can be further converted by angiotensin converting enzyme to angiotensin II (Ang II) of octapeptide which is the final physiological active substance of renin-angiotension-aldosterone system (RAS) and can induce physiological functions such as contraction of blood vessel and elevation of blood pressure by binding to specific angiotensin II (ATII) receptor.

EP0253310 discloses a series of imidazole derivatives. Research of E. I. Du Pont de Nemours and Company (US) found that a compound of DUP753 has a good effect on lowering blood pressure. It was approved in 1994 and became the first non-peptide type Ang II receptor antagonist, i.e. losartan potassium, which inhibits contraction of blood vessel by selectively blocking the actions of angiotensin II of smooth muscle in blood vessel on its Ang I receptor to achieve the functions of dilating blood vessel and reducing blood pressure.

With the development and marketing of losartan potassium, various medical R&D organizations and companies began studies on structure of Ang II receptor antagonists in succession. U.S. Pat. No. 5,196,444 discloses a series of benzimidazole derivatives and processes for preparation thereof. Such derivatives have angiotensin II antagonistic activity and antihypertensive activity and thereby can be used to treat hypertensive diseases. Among them, candesartan was developed and marketed in 1997 by Takeda Chemical Industries, Ltd. (JP), which releases ester group in vivo and is hydrolyzed to its active metabolite to exert the action of lowering blood pressure.

U.S. Pat. No. 5,616,599 discloses a series of 1-biphenylmethylimidazole derivatives whose structures are similar to that of losartan. The significant difference in structure between them is that the chlorine atom at the 4-position of the imidazole ring of losartan is converted to 1-hydroxy-1-methylethyl and the 5-position of that is converted to a carboxyl group, hydroxyl group or pro-drug structures such as ester or amide. It is demonstrated to have good activity in reducing blood pressure. Therefore, Sankyo Company, Ltd. (JP) developed and marketed a drug of olmesartan.

Compared with other Ang II receptor antagonists marketed subsequently, losartan has more tolerance, fewer side effects and fewer possibilities to cause cough or edema. Studies have suggested that it is effective for reducing serum uric acid, TC and TG, and has no adverse effect on insulin sensitivity, insulin secretion and glucose tolerance of hyperinsulinism patients and is a safe antihypertensive drug. However, only 14 percent of losartan potassium can be metabolized in vivo to its active substance of EXP3174. Although losartan potassium itself has a strong activity in reducing blood pressure, its activity is only 3 percent of that of EXP3174. Molecular polarity of EXP3174 is too strong to get through the cell membrane by passive absorption forms such as diffusion. It is necessary to change its structure to improve its passive absorption.

U.S. Pat. No. 5,298,519 discloses a 5-position carboxyl esterified product of EXP3174, emphasizes on the research of a compound HN-65021, and discloses a test result of lowering blood pressure by oral administration of HN-65021 to show the compound has an activity of lowering blood pressure similar to that of losartan (British Journal of Clinical Pharmacology, 40, 1995, 591-593), it is indicated that converting 5-position carboxyl of the imidazole ring of EXP3174 molecule to a group with a smaller polarity is a tendency of the modification of losartan. It is required to convert the structure of EXP3174 molecule for getting an active compound with a better pharmacological effect of lowering blood pressure.

In summary, there is an urgent need to develop an active compound with an excellent effect of lowering blood pressure, a high efficiency of absorption and conversion and/or a high safety in this field.

CONTENTS OF INVENTION

The present invention provides a compound of formula (I), or its pharmaceutically acceptable salts or solvates, (I)

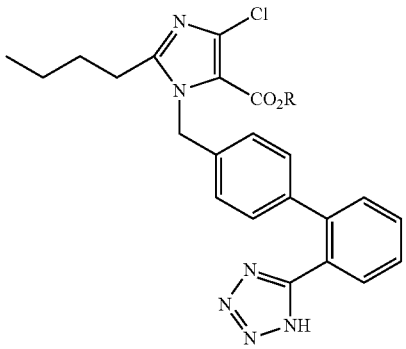

therein R is selected from straight or branched $C_1$-$C_4$ alkyl, or R is

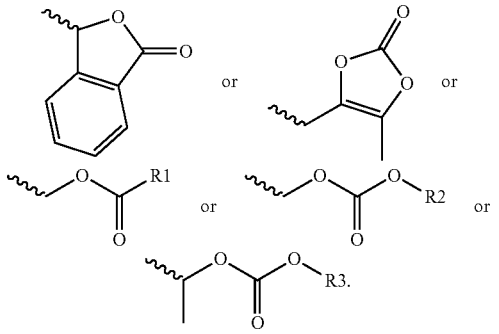

wherein R1, R2, and R3 are independently selected from the group consisting of hydrogen, straight or branched $C_1$-$C_4$ alkyl, and $C_3$-$C_7$ cycloalkyl, wherein the alkyl or the cycloalkyl in the definition of R, R1, R2, and R3 is unsubstituted or substituted by 1-3 substituents selected from the group consisting of F, Cl, Br, $NH_2$, and OH.

In a preferred embodiment of the present invention, R is selected from the group consisting of straight or branched $C_1$-$C_4$ alkyl, and preferably, R is ethyl.

In another preferred embodiment of the present invention, R is

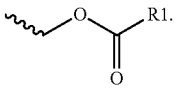

wherein R1 is selected from hydrogen, straight or branched $C_1$-$C_4$ alkyl, and $C_3$-$C_7$ cycloalkyl. Preferably, R1 is selected from straight or branched $C_1$-$C_4$ alkyl. More preferably, R1 is straight or branched butyl.

In a further preferred embodiment, R is

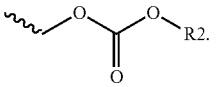

wherein R2 is selected from the group consisting of hydrogen, straight or branched $C_1$-$C_4$ alkyl, and $C_3$-$C_7$ cycloalkyl. Preferably, R2 is selected from the group consisting of straight or branched $C_2$-$C_4$ alkyl. More preferably, R2 is ethyl, isopropyl, or tert-butyl.

In another preferred embodiment of the present invention, R is

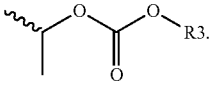

wherein R3 is selected from the group consisting of hydrogen, straight or branched $C_1$-$C_4$ alkyl, and $C_3$-$C_7$ cycloalkyl. Preferably, R3 is selected from the group consisting of straight or branched $C_3$-$C_4$ alkyl, and $C_3$-$C_7$ cycloalkyl. More preferably, R3 is isopropyl, tert-butyl, or cyclohexyl.

As described above, the straight or branched $C_1$-$C_4$ alkyl means methyl, ethyl, propyl, isopropyl, butyl, isobutyl, sec-butyl or tert-butyl; preferably methyl, ethyl, propyl, isopropyl, butyl, or tert-butyl. The $C_3$-$C_7$ cycloalkyl cyclopropyl, cyclobutyl, cyclopentyl, cyclohexyl, cycloheptyl; preferably cyclobutyl, cyclopentyl, cyclohexyl. Cyclohexyl is the most preferred.

In the present invention, the specific preferred compounds are:

2-butyl-4-chloro-1-[2'-(1H-tetrazol-5-yl)1,1'-biphenyl-methyl]imidazole-5-carboxylic acid, ethyl ester;

2-butyl-4-chloro-1-[2'-(1H-tetrazol-5-yl)1,1'-biphenyl-methyl]imidazole-5-carboxylic acid, 2-[C]-benzofuranonyl ester;

2-butyl-4-chloro-1-[2'-(1H-tetrazol-5-yl)1,1'-biphenyl-methyl]imidazole-5-carboxylic acid, cyclic 2,3-carbonate;

2-butyl-4-chloro-1-[2'-(1H-tetrazol-5-yl)1,1'-biphenyl-methyl]imidazole-5-carboxylic acid, pivaloyloxymethyl ester;

2-butyl-4-chloro-1-[2'-(1H-tetrazol-5-yl)1,1'-biphenyl-methyl]imidazole-5-carboxylic acid, 1-[(isopropoxycarbonyl)oxy]ethyl ester;

2-butyl-4-chloro-1-[2'-(1H-tetrazol-5-yl)1,1'-biphenyl-methyl]imidazole-5-carboxylic acid, 1-[(tert-butoxycarbonyl)oxy]ethyl ester;

2-butyl-4-chloro-1-[2'-(1H-tetrazol-5-yl)1,1'-biphenyl-methyl]imidazole-5-carboxylic acid, 1-[(cyclohexyloxycarbonyl)oxy]ethyl ester;

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester;

2-butyl-4-chloro-1-[2'-(1H-tetrazol-5-yl)1,1'-biphenyl-methyl]imidazole-5-carboxylic acid, 1-[(ethoxycarbonyl)oxy]methyl ester;

2-butyl-4-chloro-1-[2'-(1H-tetrazol-5-yl)1,1'-biphenyl-methyl]imidazole-5-carboxylic acid, 1-[(tert-butoxycarbonyl)oxy]methyl ester.

The present invention also provides a pharmaceutical composition comprising 0.05~50 mg of the compound of formula I or its pharmaceutically acceptable salts, and pharmaceutically acceptable carriers, excipients or diluents.

The present invention also provides a method of treating a disease, which may be alleviated or cured by inhibiting I receptors of angiotensin II, comprising the step of administrating a patient in need of such treatment with the compound of formula I or its pharmaceutically acceptable salts in the amount of 0.05-30 mg/kg weight/day.

The present invention also provides a process for the preparation of the compound of formula I, which includes the following steps:

(a). losartan potassium is oxidized to 2-butyl-4-chloro-1-[2'-(1H-tetrazol-5-yl)1,1'-biphenyl-methyl]imidazole-5-carboxylic acid;

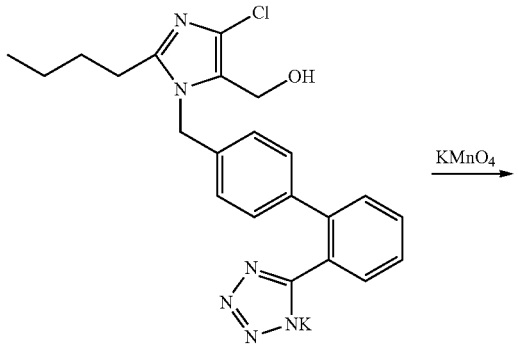

-continued

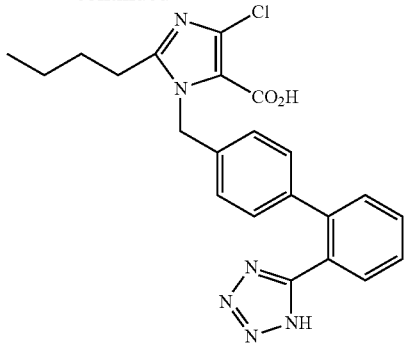

(b). the oxidative product obtained form step (a) is reacted with triphenylchloromethane to give 2-butyl-4-chloro-1-[2'-(1-triphenylmethyl-tetrazol-5-yl)1,1'-biphenyl-methyl]imidazole-5-carboxylic acid;

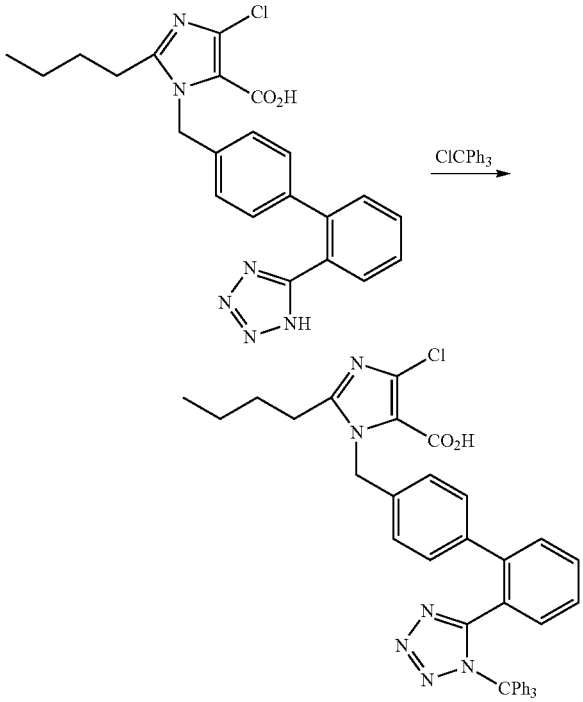

(c1). the product obtained from step (b) is reacted with the compounds of formula X—R to give esterified intermediates under alkaline condition; then the trityl is deprotected to obtain compound of formula I in which X is halogen, R represents the following groups:

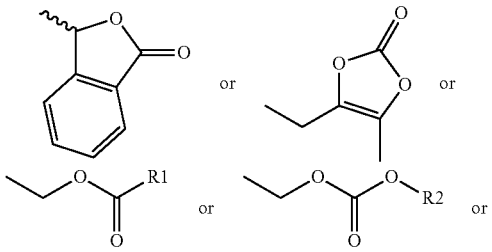

-continued

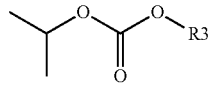

wherein, R1, R2, R3 are independently selected from the group consisting of hydrogen, straight or branched, $C_1$-$C_4$ alkyl, and $C_3$-$C_7$ cycloalkyl group.

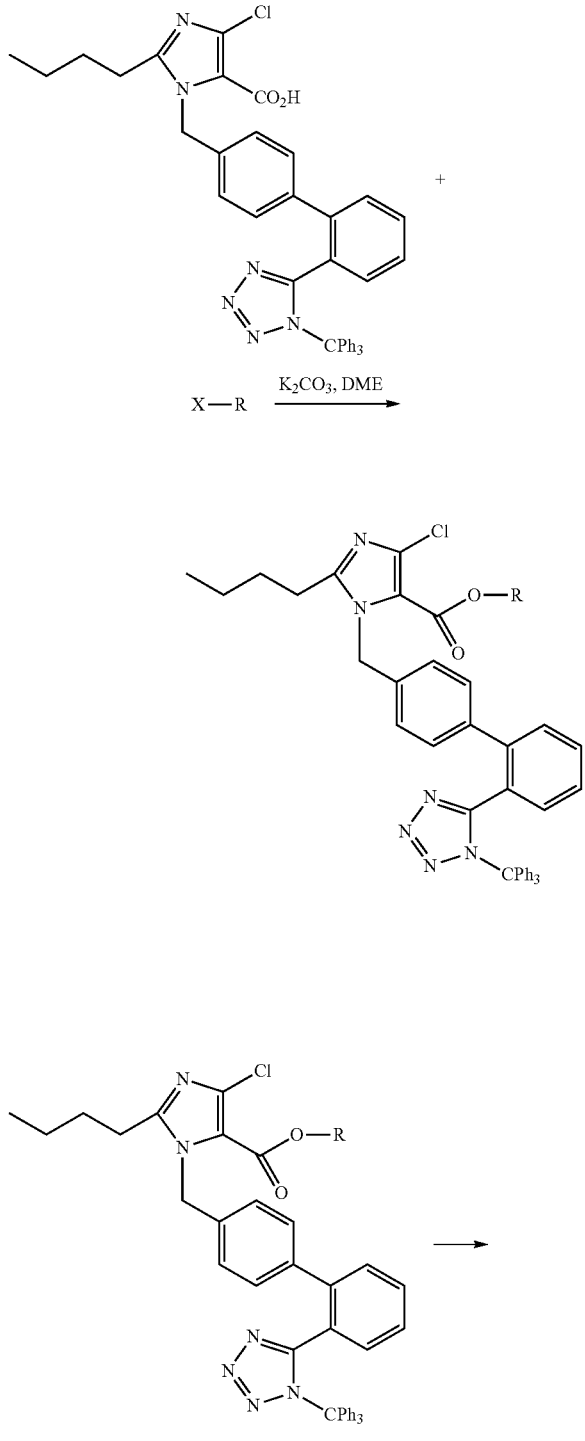

-continued

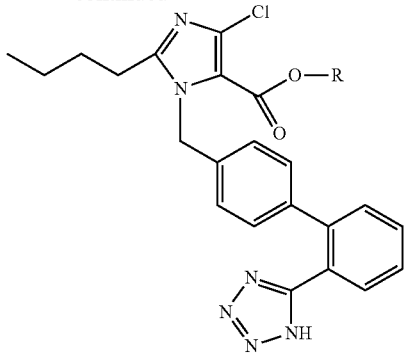

or (c2) when R is selected from the group consisting of straight or branched $C_1$-$C_4$ alkyl, the product obtained from step (b) is reacted under reflux with organic alcohol ROH(R is defined as above) in the presence of catalytic acid to obtain the compound of formula I.

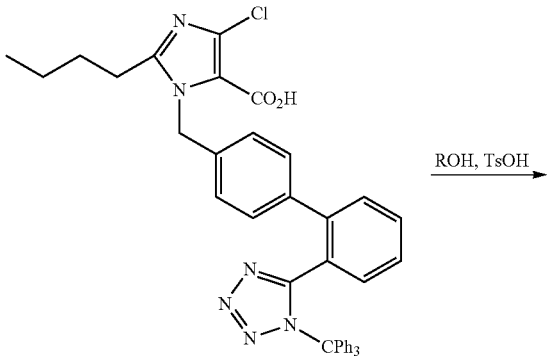

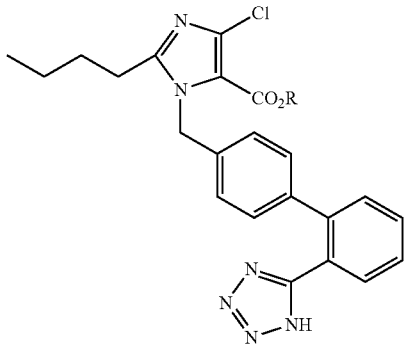

Specifically, the present invention provides a process for the preparation of the compound of formula I.

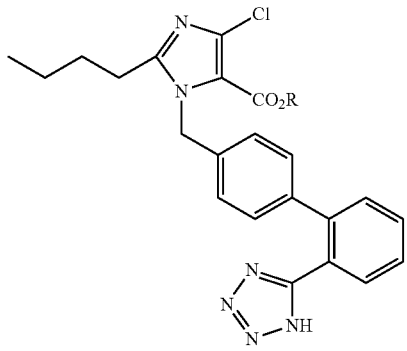

(I)

When R is selected from straight or branched $C_1$-$C_4$ alkyl, the compound can be prepared by the following method:

(a). losartan potassium is oxidized to 2-butyl-4-chloro-1-[2'-(1H-tetrazol-5-yl)1,1'-biphenyl-methyl]imidazole-5-carboxylic acid in the presence of oxidant such as $KMnO_4$:

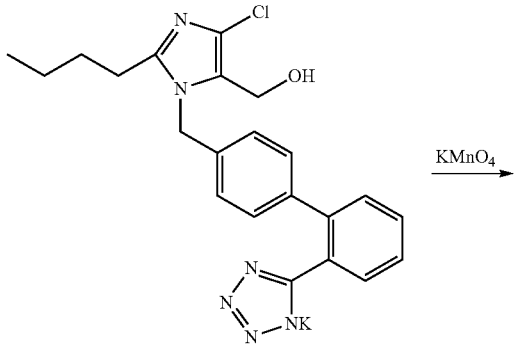

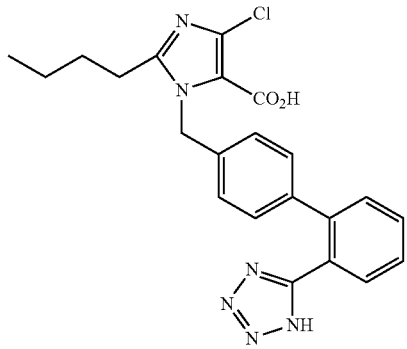

(b). the oxidative product above is reacted with triphenylchloromethane to give 2-butyl-4-chloro-1-[2'-(1-triphenylmethyl-tetrazol-5-yl)1,1'-biphenyl-methyl imidazole-5-carboxylic acid;

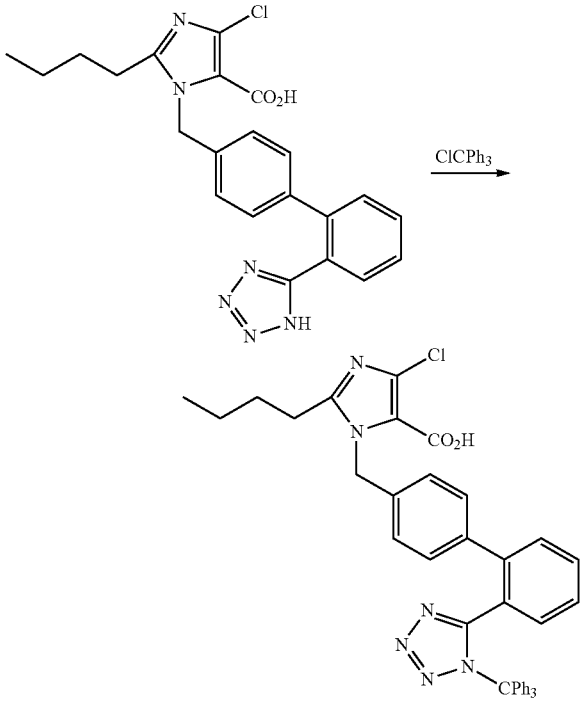

(c). to the product obtained from step (b), organic alcohol ROH(R is defined as above) and catalytic acid (organic acid such as p-toluenesulfonic acid, or inorganic acid such as hydrochloric acid, sulfuric acid and phosphoric acid) are added, reacted under reflux, extracted and concentrated to obtain the final product.

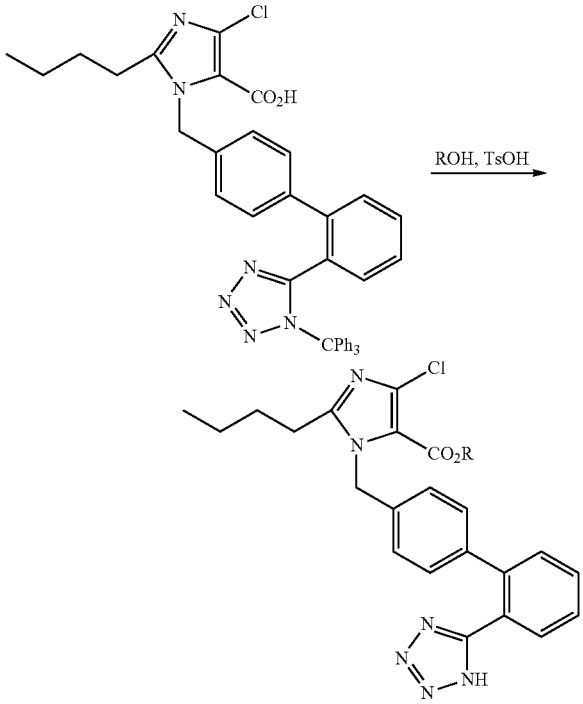

Other compounds described in the present invention can be prepared by the following method:

(a). losartan potassium is oxidized to 2-butyl-4-chloro-1-[2'-(1H-tetrazol-5-yl)1,1'-biphenyl-methyl]imidazole-5-carboxylic acid in the presence of oxidant such as KMnO4;

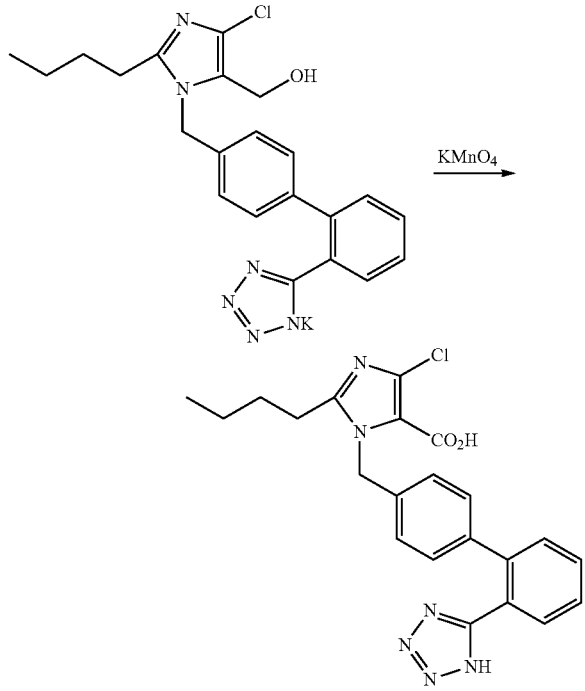

(b). the oxidative product above is reacted with triphenylchloromethane to give 2-butyl-4-chloro-1-[2'-(1H-triphenylmethyl-tetrazol-5-yl)1,1'-biphenyl-methyl]imidazole-5-carboxylic acid;

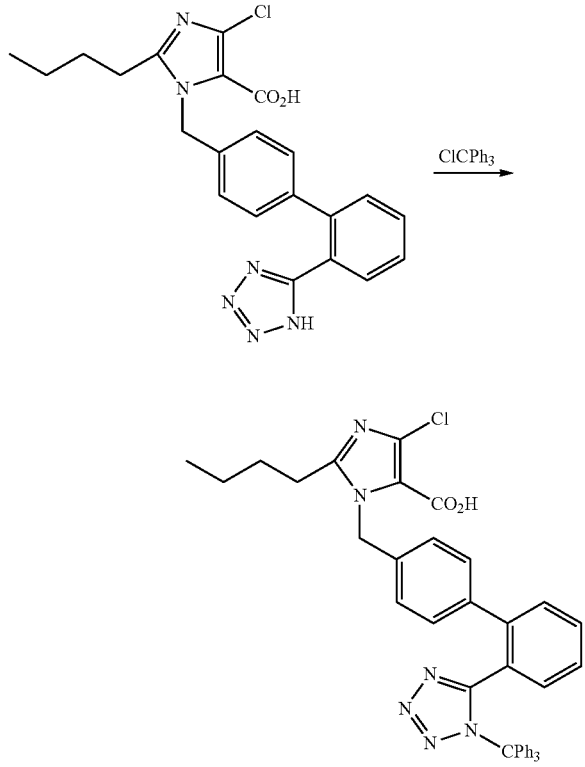

(c). the product from the above step (b) is reacted with the compounds of formula X—R to give esterified intermediates under alkaline condition (such as potassium carbonate and N,N-dimethylacetamide (DME) or N,N-dimethylforamide (DMF)); wherein X is halogen, preferably fluorine, chlorine, bromine. R represents the following structures:

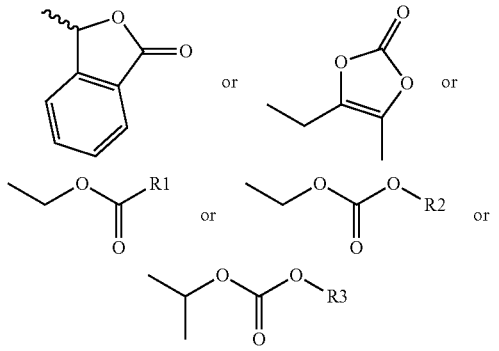

wherein, R1, R2, and R3 are independently selected from the group consisting of hydrogen, straight or branched $C_1$-$C_4$ alkyl, and $C_3$-$C_7$ cycloalkyl.

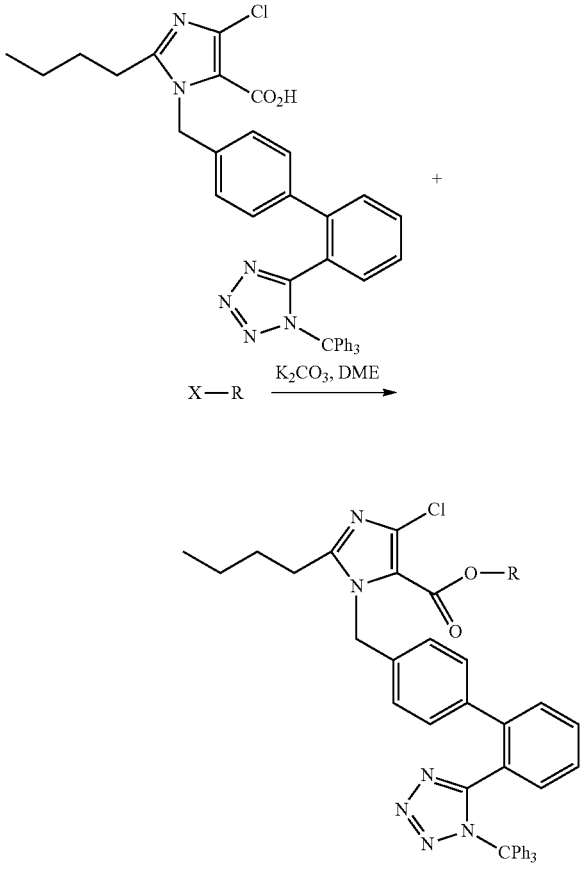

(d). the esterified intermediates from the step (c) are deprotected to remove the triphenylmethyl group in the presence of acids or alcohols (such as methanol, or ethanol) and purified to give the final products.

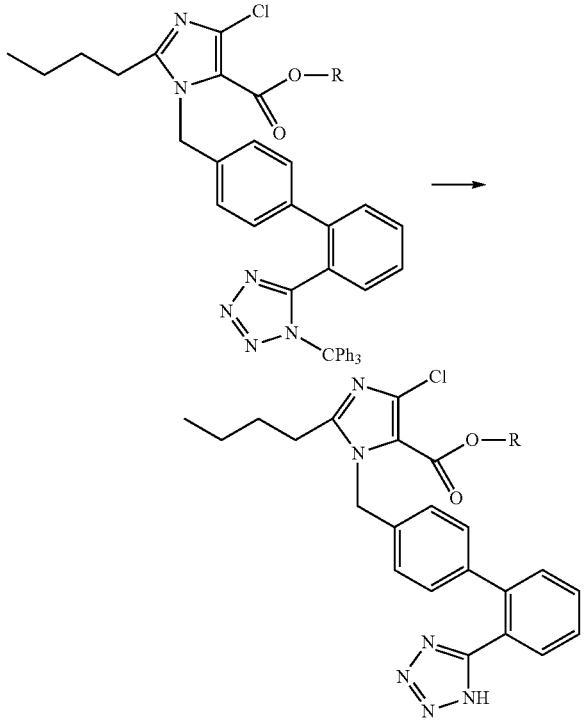

In the preparation schemes above, all the reactions are carried out between −10° C. to the reflux temperature, typically between the room temperature (about 25° C.) to the reflux temperature. Preferably, the temperature of reaction is 5° C. to 100° C.; and more preferably 20 to 80° C. The reaction time is not limited, generally from one minute to 24 hours, preferably 1-20 hours. A solvent for the preparation is generally an inert solvent such as water, DMF, or alcohol (such as methanol, ethanol, or isopropanol and the like).

The compound obtained according to the method of the invention can be administered to human beings orally, rectally, parenterally (intravenously, intramuscularly or subcutaneously), locally (powders, ointments or drops). Said compound can be administered alone or in combination with other pharmaceutically acceptable compounds. Note that the compounds according to the invention can be administered as a mixture.

Solid dosage forms for oral administration may include capsules, tablets, pills, powders and granules. In such solid dosage forms, the active compound may be mixed with at least one conventional inert excipients (or carriers) such as citrate sodium, dicalcium phosphate, or with the following components: (a) fillers or compatibilizers, for example, starch, lactose, sucrose, glucose, mannitol and silicic acid; (b) binders, for example, hydroxymethylcellulose, alginate, gelatin, polyvinylpyrrolidone, sucrose, amine gum; (c) humectants, for example, glycerin; (d) disintegrants, for example, agar, calcium carbonate, potato starch or cassava starch, alginic acid, some composite silicate and sodium carbonate; (e) slow-dissolving agents, for example, wax, (f) sorbefacients, for example, quaternary ammonium compound; (g) wetting agents, for example, cetyl alcohol and glycerin monostearate; (h) adsorbents, for example, kaolin; and (i) lubricants, for example, talc, calcium stearate, magnesium stearate, solid polyethylene glycol, sodium dodecyl sulfate or mixture thereof. Dosage forms such as capsules, tablets and pills may include bufferings.

Solid dosage forms, such as tablets, rotulas, capsules, pills and granules may be prepared with coatings or shells such as enteric coatings or other materials known by those skilled in the art. They can include opaque agent. Furthermore, active compounds or compounds in the composition can be slow-released in a part of alimentary canal. Examples of embedding components include polymer substance and wax substance. If necessary, the active compounds also can be combined with one or more or excipients above to make a form of micro-capsule.

Liquid dosage forms for oral administration may include pharmaceutically acceptable emulsions, solutions, suspensions, syrups or tinctures. Beside active compounds, the liquid dosage form may include inert diluents conventionally used in this field, such as water or other solvents, solubilizing agents and emulsifying agents, such as ethanol, isopropanol, ethyl carbonate, ethyl acetate, propylene glycol, 1,3-butanediol, dimethylformamide and oil, particularly cottonseed oil, peanut oil, corn germ oil, olive oil, caster oil and sesame oil or mixtures or these substances.

Beside the inert diluents, the composition may also include auxiliary agents such as wetting agents, emulsifying agents and suspending agents, sweetening agents, flavorings and flavors.

Beside the active compounds, the suspensions may include suspending agents, for example, ethoxylated isooctadecanol, polyoxyethylene sorbitol, and dehydrated sorbate, microcrystalline cellulose, methanol aluminum and agar or mixtures of these substances.

Compositions for parenteral injection may include physiologically acceptable sterile solutions, dispersions, suspensions or emulsions with or without water, and sterile powders for reconstituting into sterile injection solutions or dispersions. Appropriate carriers, diluents, solvents or excipients with or without water may include water, ethanol, polyalcohol and appropriate mixtures thereof.

Dosage form of the compounds of the invention for local administration may include ointments, powder, sprays and inhalants. The active components is mixed with physiologically acceptable carriers and any antiseptics, buffers, or required propellants if necessary under sterile condition.

In the present invention, the term "pharmaceutically acceptable salts" means relatively innocuous inorganic acid addition salts or organic acid addition salts of the compound of the present invention. These salts may be prepared in situ during the final isolation and purification of the compounds; alternatively, prepared by reacting the purified compounds in a form of free alkali with appropriate organic or inorganic acids and separating the salts from the reactants. Representative salts includes hydrobromide, hydrochloride, sulfate, sulphite, acetate, oxalate, pentanoate, oleate, palmate, stearate, laurate, borate, benzoate, lactate, phosphate, toluene formate, citrate, maleate, fumarate, succinate, tartrate, benzoate, methanesulfonate, gluconate, lactobionate and dodecylsulfonate and the like. They may contain cations based on alkali metals and alkali-earth metals, such as sodium, lithium, potassium, calcium, magnesium and the like, and cations of innocuous amine, quarternary amine, and amine cations, including but not limited to amine, tetramethyl amine, tetraethyl amine, methyl amine, dimethyl amine, trimethyl amine, tri-ethylamine, ethylamine and the like.

It is proved by animal tests that the compounds in accordance with the present invention have an effect of lowering blood pressure, and can be used for preparation of medicines to treat high blood pressure. The effect for lowering blood pressure of the compounds of the invention may be determined by conventional methods. A preferred evaluating method is described as follow:

A female spontaneously hypertensive rat (SHR) is anaesthetize by abdominal cavity injection with diazepam of 5 mg/kg and ketamine hydrochloride of 50 mg/kg and its back is fixed. An artery conduit is inserted from the left of a femoral artery to a lower abdominal aorta, and then a stomach fistula treatment is operated. After 20-30 hours for postoperative recovery, the artery conduit is connected to a pressure transducer by a perfusion three-way tube. Blood pressure signals per pulse are transformed into biologic signals by the pressure transducer, and systolic blood pressures and diastolic blood pressures per pulse are real-time recorded by a computer. After the SHR is connected to the computer system for 4-5 hours, blood pressures and palpitation intervals in one hour are recorded as normal comparing data before administration. Afterwards, the medicine with a dosage of 30 mg/kg and a volume of 2 ml/kg is administrated through the stomach fistula. Blood pressures in 6 hours after administration are continuously recorded to observe change of systolic blood pressure and diastolic blood pressure.

The present invention has the following advantage: compared with the conventional Ang II receptor antagonists, the compounds of the invention have low toxicity and high efficiency of conversion with an equal effect of lowering blood pressure.

The invention is further illustrated by the following examples. It is appreciated that these examples are only intended to illustrate the invention, but not to limit the scope of the invention. For the experimental methods in the following examples, they are performed under routine conditions, or as instructed by the manufacturers, unless otherwise specified. Unless otherwise indicated, the amounts and percents are by weight.

MODE OF CARRYING OUT THE INVENTION

The following examples are merely illustrative of the invention and are not intended to limit the scope of the invention.

Example 1

2-butyl-4-chloro-1-[2'-(1H-tetrazol-5-yl)1,1'-biphenyl-methyl]imidazole-5-carboxylic acid

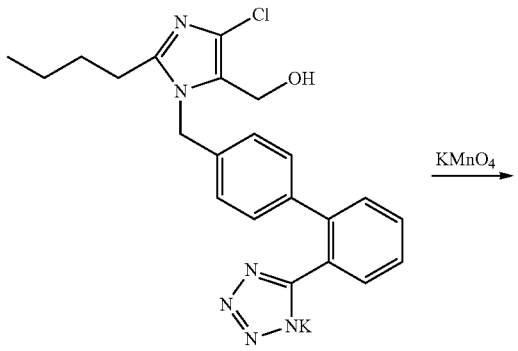

-continued

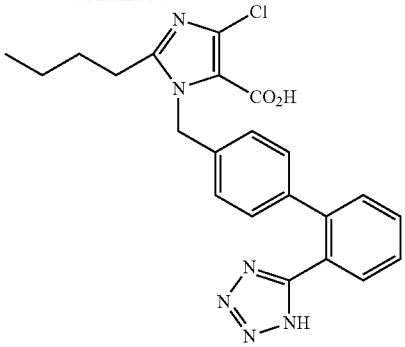

4.57 g of 2-butyl-4-chloro-1-[2'-(1H-tetrazol-5-yl)1,1'-biphenyl-methyl]-5-hydroxymethyl-imidazole was dissolved in 10 ml of water and cooled to −5° C.~0° C. The solution of 1.58 g of $KMnO_4$ in 130 ml of water was added dropwise to the resulting solution. After this, the mixture was reacted for 16 hours at 50° C. The reaction was stopped and the reaction mixture was filtered. 50 ml of 1 mol/L $NaS_2O_3$ was added to the filtrate. The resulting solution was adjusted to pH 2-3 using diluted hydrochloric acid and went turbid. The solution was extracted with ethyl acetate, dried, concentrated and flash chromatographed using a mixture of petroleum ether and ethyl acetate (1:6 by volume) as the mobile phase, to give 3.85 g of a white solid with a yield of 89.1%.

$^1$H-NMR ($CDCl_3$) δ H (ppm): 0.801 (3H, t, J=3.6), 25 (2H, m, J=3.5), 1.49 (2H, m, J=5), 2.56 (2H, t, J=3.5), 5.58 (2H, s), 6.94-7.08 (4H, m, J=5), 7.65-7.50 (2H, m, J=8.5)

ESI (−) m/z: 435.1

Mp: 125.2~128.5° C.

-continued

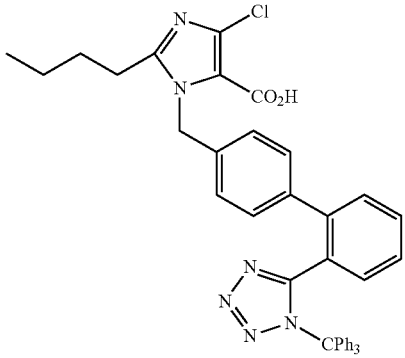

To a 100 ml of one-necked flask, 4.36 g of 2-butyl-4-chloro-1-[2'-(1H-tetrazol-5-yl)1,1'-biphenyl-methyl]imidazole-5-carboxylic acid, 15 ml of N,N-dimethylformamide, 1.66 g of potassium carbonate and 2.78 g of triphenylchloromethane were added in turn. The mixture was reacted at room temperature overnight. The reaction was stopped and 100 ml of water was added. The resulting mixture was extracted with 100 ml of ethyl acetate and washed once by saturated brine. The organic phase was dried and concentrated to give 7.5 g of 2-butyl-4-chloro-1-[2'-(1H-triphenylmethyl-tetrazol-5-yl)1,1'-biphenyl-methyl]-imidazole-5-carboxylic acid as a yellow oil. The crude product obtained from this example was used as material referred to in the following examples without purification.

Example 2

2-butyl-4-chloro-1-[2'-(1H-triphenylmethyl-tetrazol-5-yl)1,1'-biphenyl-methyl]imidazole-5-carboxylic acid

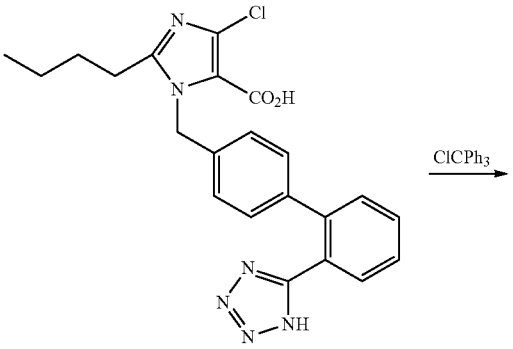

Example 3

2-butyl-4-chloro-1-[2'-(1H-tetrazol-5-yl)1,1'-biphenyl-methyl]imidazole-5-carboxylic acid, ethyl ester (compound 1)

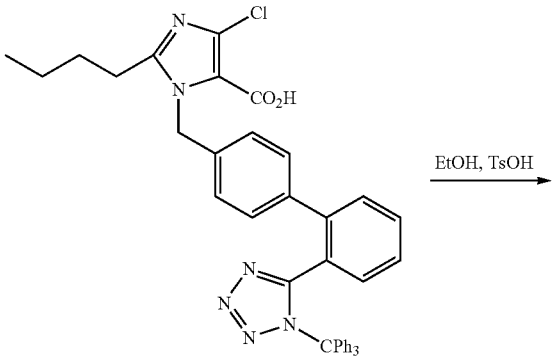

-continued

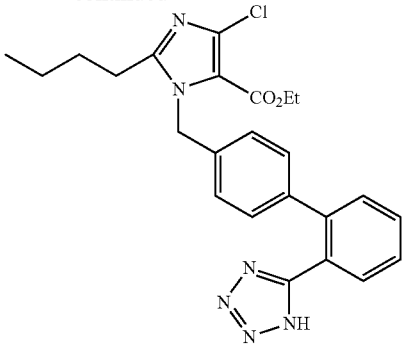

1

To 678.5 mg of material, 15 ml of anhydrous ethanol and 312 mg of p-toluenesulfonic acid (TsOH) were added. The mixture was refluxed for 6 hours. At the end of the reaction, 30 ml of water was added. The resulting mixture was extracted with 30 ml of ethyl ether. The organic phase was dried and concentrated to give 274 mg of 2-butyl-4-chloro-1-[2'-(1H-tetrazol-5-yl)1,1'-biphenyl-methyl]imidazole-5-carboxylic acid, ethyl ester as a colorless oil product with a yield of 59%.

$^1$H-NMR ($CDCl_3$) δ H (ppm): 0.80-0.85 (m, 6H, J=13.6), 1.26 (m, 2H, J=20.2), 1.38 (H, t, J=14.8), 1.58 (m, 2H, J=7.5), 2.69 (q, 2H, J=24.5), 5.44 (s, 2H), 6.94-7.50 (8H), 8.10 (d, 1H, J=6.14)

ESI (+) m/z: 465.1

Example 4

(+/−)2-butyl-4-chloro-1-[2'-(1H-tetrazol-5-yl)1,1'-biphenyl-methyl]imidazole-5-carboxylic acid, 2-[C]-benzofuranonyl ester (compound 2)

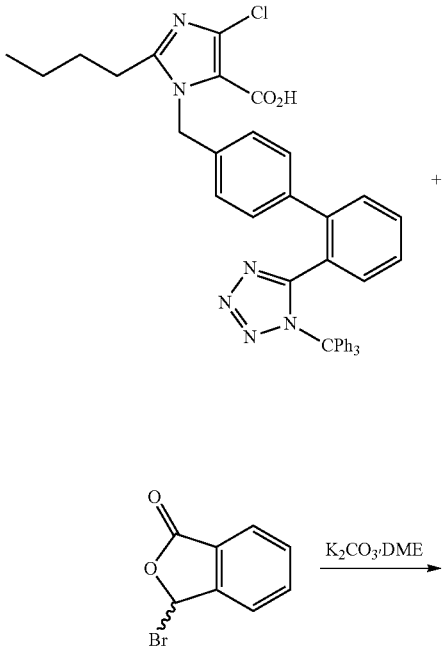

-continued

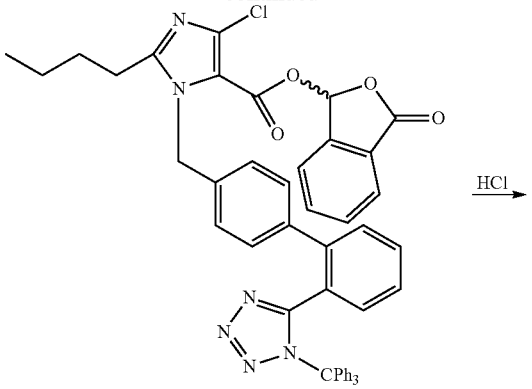

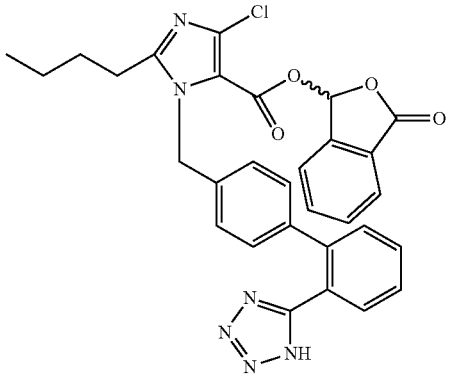

2

678.5 mg of material was dissolved in 8 ml of N,N-dimethylacetamide, then 0.172 g of potassium carbonate and 263 mg of 7-bromo-2-benzofuranone were added in turn. The mixture was reacted at 40-45° C. for 4 hours. At the end of the reaction, 30 ml of water was added. The resulting mixture was extracted twice with 25 ml of ethyl ether. The organic phase was dried and concentrated to give 606.4 mg of esterified intermediate with a yield of 75%. The intermediate was dissolved in 15 ml of dioxane and 4 ml of 4N HCl was added. The mixture was reacted at room temperature for 16 hours. The resulting solution was poured into water, extracted with ethyl acetate, dried, concentrated and flash chromatographed (eluent: ethyl acetate/petroleum ether=1/2) to give 284.7 mg of pure product (+/−)2-butyl-4-chloro-1-[2'-(1H-tetrazol-5-yl)1,1'-biphenyl-methyl]imidazole-5-carboxylic acid, 2[C]-benzofuranonyl ester with a yield of 67%.

$^1$H-NMR (DMSO-$d_6$) δ H (ppm): 0.88 (t, 3H, J=21.6), 1.26 (m, 4H, J=29.6), 1.58 (m, 2H, J=30.5), 2.50 (t, 2H, J=15.5), 5.34 (s, 2H), 6.95-7.63 (12H), 8.06 (d, 2H, J=9.1)

ESI (+) m/z: 569.5

Mp: 120.6-124.6° C.

Example 5

2-butyl-4-chloro-1-[2'-(1H-tetrazol-5-yl)1,1'-biphenyl-methyl]imidazole-5-carboxylic acid, cyclic 2,3-carbonate (compound 3)

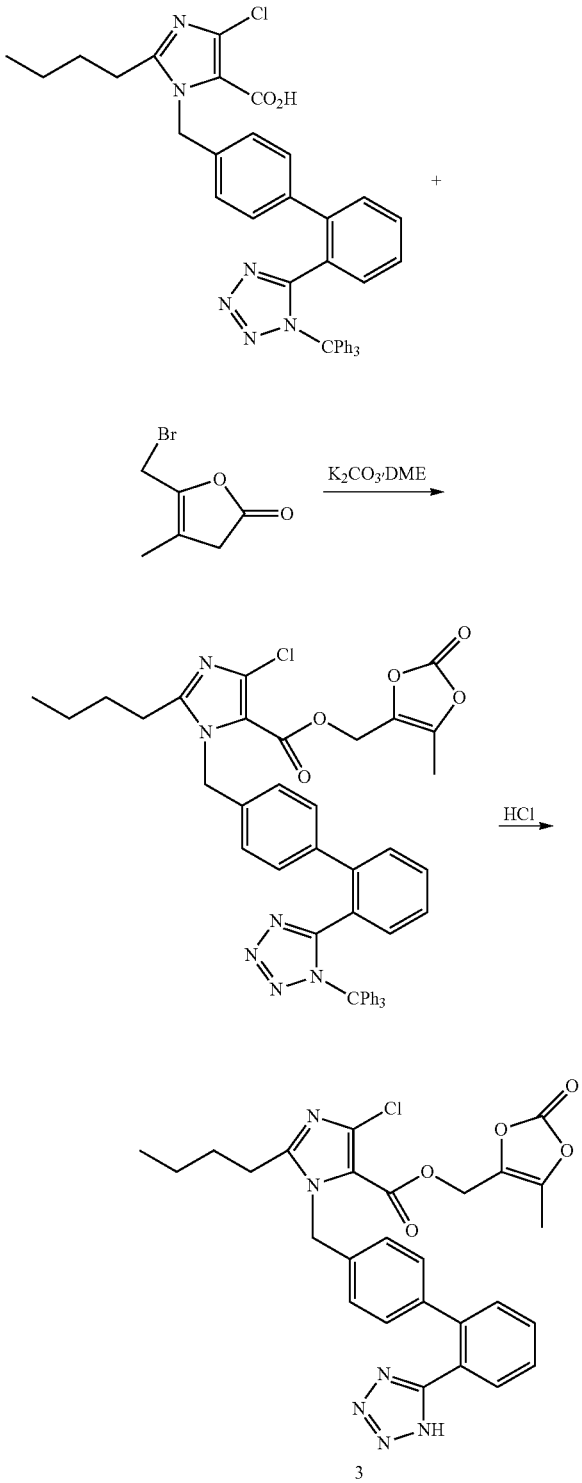

616.4 mg of material was dissolved in 8 ml of N,N-dimethylacetamide, then 0.169 g of potassium carbonate and 257 mg of 4-bromomethyl-5-methyl-2,3-carbonate were added in turn. The mixture was reacted at 40-45° C. for 4 hours. At the end of the reaction, 30 ml of water was added. The resulting mixture was extracted twice with 25 ml of ethyl ether. The organic phase was dried and concentrated to give 596.8 mg of esterified intermediate. The intermediate was dissolved in 15 ml of dioxane and 4 ml of 4N HCl was added. The mixture was reacted at room temperature for 16 hours. The resulting solution was poured into water, extracted with ethyl acetate, dried, concentrated and flash chromatographed (eluent: ethyl acetate/petroleum ether=1/2) to give the colorless oil product with a yield of 44.2%.

$^1$H-NMR (DMSO-$d_6$) δ H (ppm): 0.89 (t, 3H, J=17.5), 1.27 (m, 2H, J=11.0), 1.41 (m, 2H, J=9.9), 1.58 (t, 2H, J=7.5), 2.08 (s, 3H), 2.60 (t, 2H, J=17.5), 5.25 (s, 2H), 6.86-7.04 (8H), 8.15 (d, 1H, J=6.64)

ESI (+) m/z: 549.1

Example 6

2-butyl-4-chloro-1-[2'-(1H-tetrazol-5-yl)1,1'-biphenyl-methyl]imidazole-5-carboxylic acid, pivaloyloxymethyl ester (compound 4)

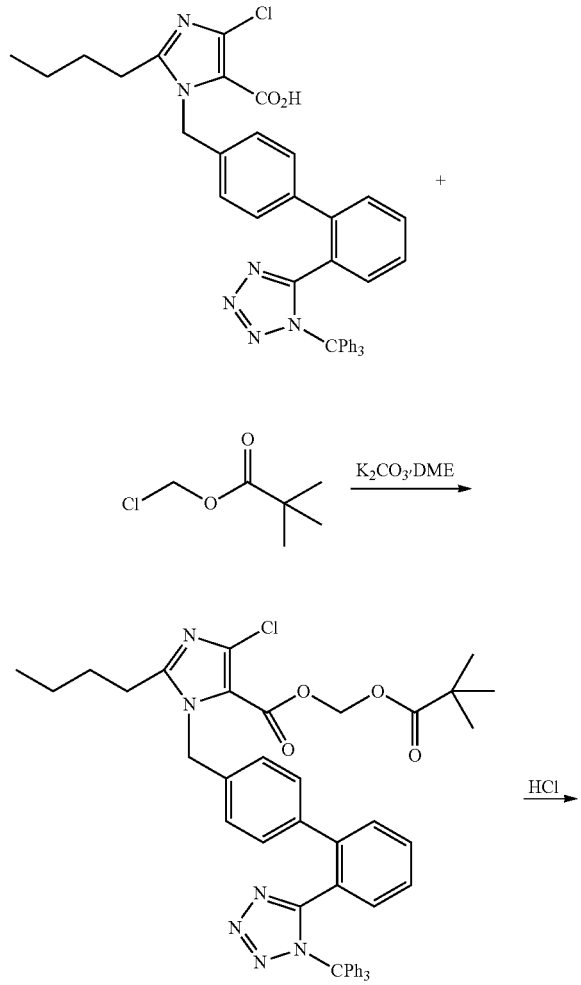

-continued

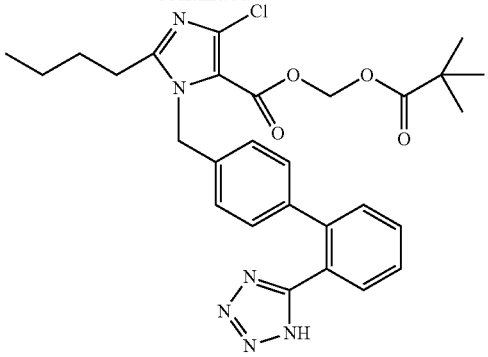

4

To 407.1 mg of material, 5 ml of N,N-dimethylacetamide, 0.124 g of potassium carbonate were added. The mixture was stirred at room temperature for 10 minutes. Then 0.18 g of chloromethyl pivalate was added and stirred for 10 minutes. The mixture solution was heated to 45-50° C., reacted for 16 hours. The progress of the reaction was monitored by TLC (eluent: ethyl acetate/petroleum ether=1/1). Insoluble substance was removed by filtration, and 50 ml of water was added to obtain the white emulsion. The resulting mixture was extracted with 50 ml ethyl acetate. The organic phase was washed with saturated brine, dried, concentrated and flash chromatographed to give 0.273 g of intermediate. 15 ml of dioxane and 5 ml of 4 mol/L HCl were added, and the mixture was reacted at room temperature for 16 hours. The reaction was stopped and the solution was adjusted to pH 6-7 using aqueous sodium bicarbonate solution. The solution went turbid and was extracted with saturated brine, dried, concentrated to give 0.242 g of oil 2-butyl-4-chloro-1-[2'-(1H-tetrazol-5-yl)1,1'-biphenyl-methyl]imidazole-5-carboxylic acid, pivaloyloxymethyl ester.

$^1$H-NMR ($CDCl_3$) δ H (ppm): 0.89 (s, 12H), 1.21 (t, 3H, J=16.9), 1.32 (m, 2H, J=17.5), 1.54 (m, 2H, j=8.1), 4.15 (s, 2H), 5.50 (s, 2H), 6.82-7.43 (8H), 8.17 (d, 1H, J=6.8)

ESI (−) m/z: 547.6

Example 7

1-chloroethyl isopropyl carbonate

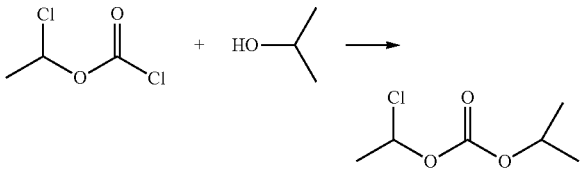

0.66 g of isopropanol was added to 1.43 g of 1-chloroethyl chloroformate, and the solution was cooled to 0° C. in an ice-water bath. The mixture of 0.84 g of pyridine and 10 ml ethyl ether was added dropwise into the solution. The solution was reacted for 1 hour at that temperature, following 4 hours at room temperature. The reaction was stopped and the mixture was filtered, and the filtrate was washed respectively with 10% hydrochloric acid and water once. The organic phase was dried and concentrated to give 1.461 g of a light yellow liquid 1-chloroethyl isopropyl carbonate with a yield of 87.7%. The crude was directly used in the next reaction without purification.

Example 8

2-butyl-4-chloro-1-[2'-(1H-tetrazol-5-yl)1,1'-biphenyl-methyl]imidazole-5-carboxylic acid, 1-[(isopropoxycarbonyl)oxy]ethyl ester (compound 5)

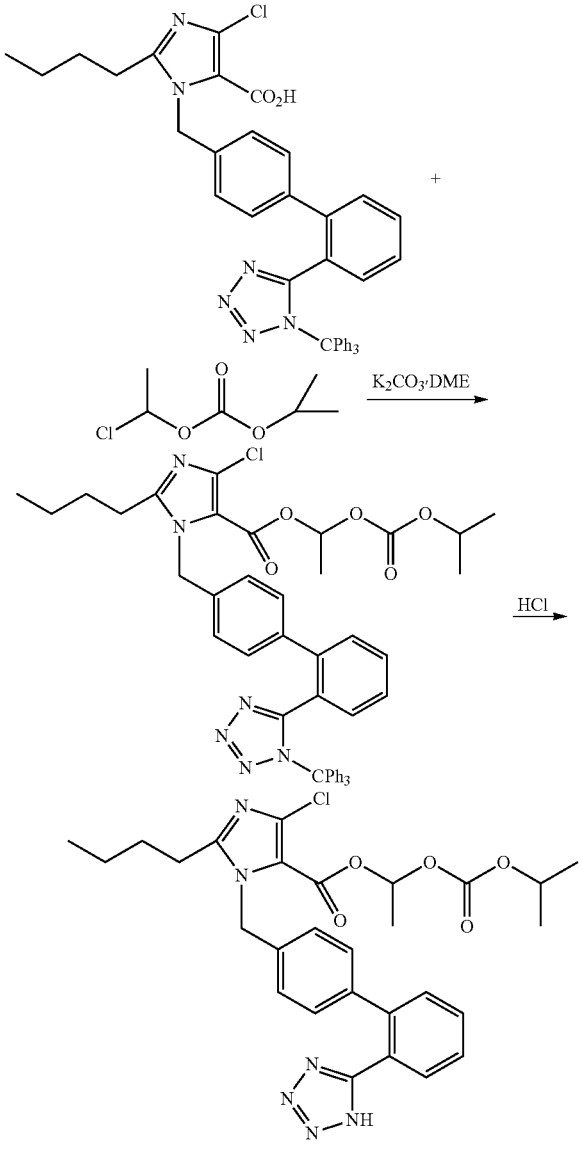

5

To a 100 ml of one-necked flask, 0.678 g of material, 0.152 g of potassium carbonate, 5 ml of N,N-dimethylacetamide were added in turn. The solution was stirred at room temperature for 20 minutes. 0.666 g 1-chloroethyl isopropyl carbonate was added and the mixture was reacted at 45-50° C. for 16 hours. After the reaction was completed, the resulting solution was filtered, and 30 ml of water was added into the filtrate. The resulting mixture was extracted with 30 ml of ethyl acetate twice. The organic phase was dried and concentrated to give 1.831 g of oil, which was directly used in the next reaction without purification.

10 ml of dioxane and 5 ml of 4 mol/L HCl were added and the mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.388 g of 2-butyl-4-chloro-1-[2'-(1H-tetrazol-5-yl)1,1'-biphenyl-methyl]imidazole-5-carboxylic acid, 1-[(isopropoxycarbonyl)oxy]ethyl ester, $^1$H-NMR ($CDCl_3$) δ H (ppm): 0.86 (t, 3H, J=12.4), 1.21 (d, 6H, J=22.8), 1.32 (m, 2H, J=38.1), 1.54 (m, 3H, J=15.7), 1.63 (m, 2H, J=7.9), 2.26 (m, 1H, J=16.2), 4.15 (q, 1H), 5.50 (s, 2H), 6.82-7.64 (8H), 8.01 (d, 1H, J=7.7)

ESI (−) m/z: 556.1

Example 9

2-butyl-4-chloro-1-[2'-(1H-tetrazol-5-yl)1,1'-biphenyl-methyl]imidazole-5-carboxylic acid, 1-[(tert-butoxycarbonyl)oxy]ethyl ester (compound 6)

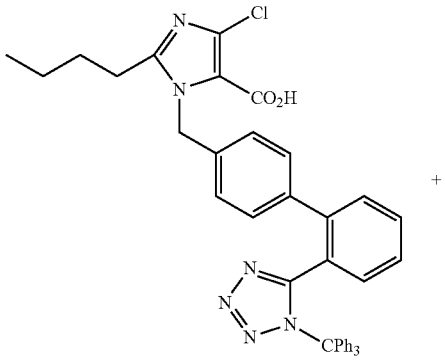

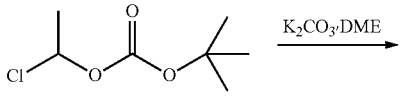

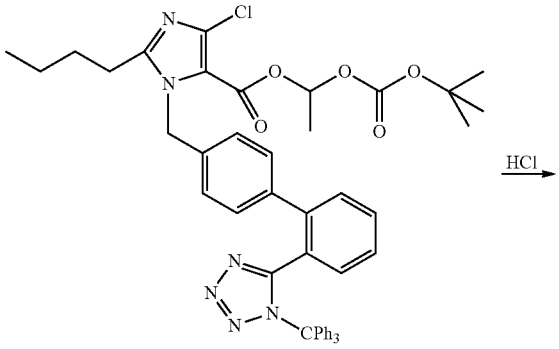

-continued

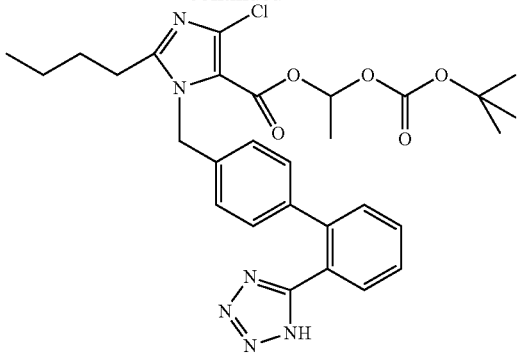

6

To a 100 ml of one-necked flask, 0.625 g of material, 0.146 g of potassium carbonate, 5 ml of N,N-dimethylacetamide were added in turn. The solution was stirred at room temperature for 20 minutes. 0.624 g of 1-chloroethyl tert-butyl carbonate was added and the mixture was reacted at 45-50° C. for 16 hours. After the reaction was completed, the resulting solution was filtered, and 30 ml of water was added into the filtrate. The resulting mixture was extracted with 30 ml of ethyl acetate twice. The organic phase was dried and concentrated to give 1.561 g of oil, which was directly used in the next reaction without purification.

10 ml of dioxane and 5 ml of 4 mol/L HCl were added and the mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.358 g of 2-butyl-4-chloro-1-[2'-(1H-tetrazol-5-yl)1,1'-biphenyl-methyl]imidazole-5-carboxylic acid, 1-[(tert-butoxycarbonyl)oxy]ethyl ester.

$^1$H-NMR ($CDCl_3$) δ H (ppm): 0.87 (s, 9H, J=14.7), 1.21 (t, 3H, J=22.5), 1.41 (m, 2H, J=39.7), 1.59 (q, 2H, J=15.6), 2.04 (q, 1H), 2.66 (4.2H, J=15.7), 4.15 (q, 3H, J=21.3), 5.50 (s, 2H), 6.82-7.64 (8H), 8.06 (d, 1H, J=8.9)

ESI (−): 551.3

Mp: 60.5-62° C.

Example 10

(+/−)2-butyl-4-chloro-1-[2'-(1H-tetrazol-5-yl)1,1'-biphenyl-methyl]imidazole-5-carboxylic acid, 1-[(cyclohexyloxycarbonyl)oxy]ethyl ester (compound 7)

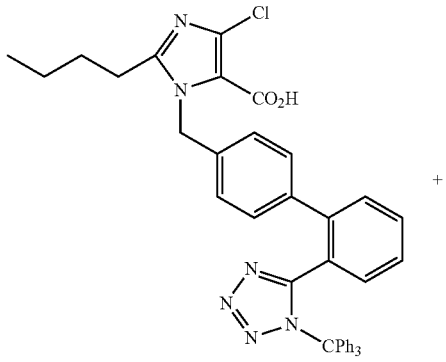

-continued

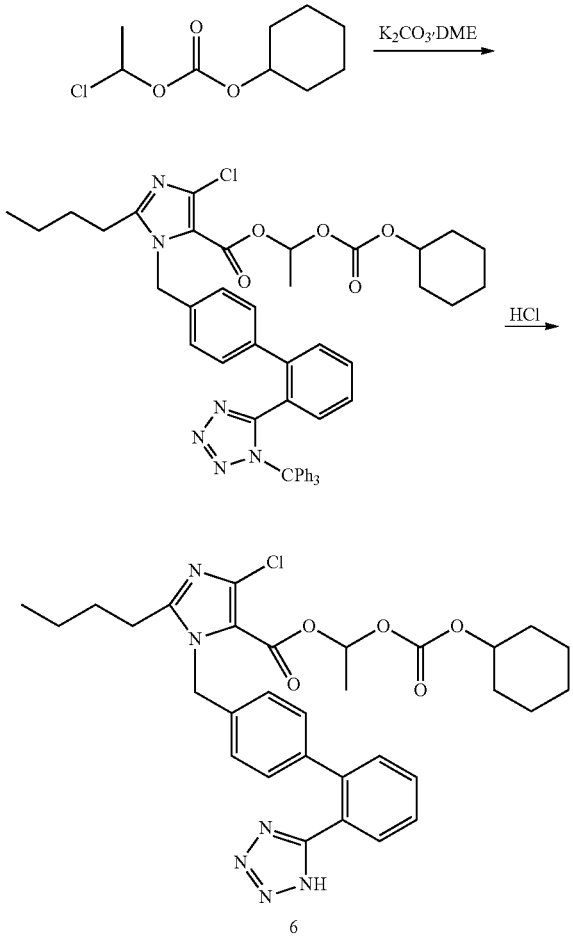

To a 100 ml of one-necked flask, 0.662 g of material, 0.161 g of potassium carbonate, 5 ml of N,N-dimethylacetamide were added in turn. The solution was stirred at room temperature for 20 minutes. 0.584 g of 1-chloroethyl cyclohexyl carbonate was added and the mixture was reacted at 45-50° C. for 16 hours. After the reaction was completed, the resulting solution was filtered, and 30 ml of water was added into the filtrate. The resulting mixture was extracted with 30 ml of ethyl acetate twice. The organic phase was dried and concentrated to give 1.456 g of oil, which was directly used in the next reaction without purification.

10 ml of dioxane and 5 ml of 4 mol/L HCl were added to react at room temperature for 16 hours. The solution was adjusted to pH 6-7 using aqueous sodium bicarbonate solution. The solution went turbid, and was extracted with ethyl acetate. The organic phase was washed with saturated brine, dried, concentrated to give 0.412 g of the final product.

$^1$H-NMR ($CDCl_3$) δ H (ppm): 0.87 (t, 3H, J=14.1), 1.2-1.6 (m, 15H), 1.73 (m, 2H, J=7.5), 2.07 (s, 1H), 2.69 (t, 2H, J=13.1), 4.05 (q, 3H, J=22.0), 5.54 (s, 2H), 6.80-7.70 (8H), 8.08 (d, 1H, J=8.6)

ESI (−) m/z: 605.7

Example 11

1-chloromethyl isopropyl carbonate

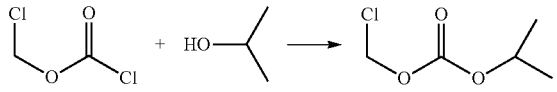

1.32 g of isopropanol was added to 2.63 g of chloromethyl chloroformate, then 20 ml of ethyl ether was added and the mixture solution was cooled to 0° C. The solution of 1.659 g of pyridine in 10 ml of ethyl ether was added into the solution, and the mixture was reacted for 1 hour at that temperature, and then reacted at room temperature for 5 hours. The reaction was stopped, and the filtrate was washed respectively with diluted hydrochloric acid and water once. The organic phase was dried and concentrated to give crude 1-chloromethyl isopropyl carbonate, which was directly used in the next reaction without purification.

Example 12

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester (compound 8)

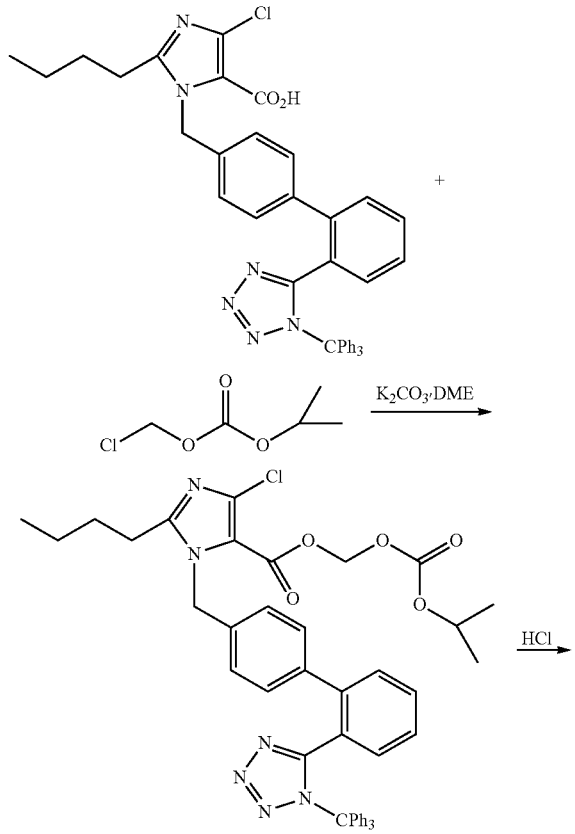

-continued

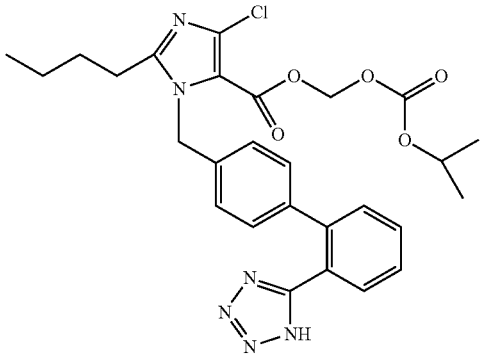

8

To a 100 ml of one-necked flask, 0.523 g of material, 0.124 g of potassium carbonate, 5 ml of N,N-dimethylacetamide were added in turn. The solution was stirred at room temperature for 20 minutes. Then 0.562 g of 1-chloromethyl isopropyl carbonate was added and the mixture was reacted at 45-50° C. for 16 hours. After the reaction was completed, the mixture solution was filtered, and 30 ml of water was added into the filtrate. The resulting mixture was extracted with 30 ml of ethyl acetate twice. The organic phase was dried and concentrated to give 1.724 g of oil, which was directly used in the next reaction without purification.

10 ml dioxane and 5 ml of mol/L HCl were added, and the resulting mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.436 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester.

In addition, the following reaction condition can be used to deprotect the protecting group. To 1.7 g of oily product, 5 ml absolute methanol was added and the mixture was heated slowly to reflux and stirred for 8 hours. When the insoluble solid disappeared totally, the mixture was discontinued to heating and cooled to 5° C. The white solid precipitated, and was separated by filtration, and the filter cake was washed with a small quantity of methanol. The combined filtrate was concentrated to dryness to give 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester with the yield of 70%.

$^1$H-NMR ($CDCl_3$) δ H (ppm): 0.89 (t, 3H, J=14.6), 1.24 (d, 6H, J=6.3), 0.37 (m, 2H, J=22.1), 1.69 (m, 2H, J=30.5), 2.64 (t, 2H, J=15.5), 4.81 (m, 1H, J=12.4), 5.54 (s, 2H), 5.86 (s, 2H), 6.95-7.64 (8H), 8.08 (d, 1H, J=7.42)

ESI (+) m/z: 552.7

Mp: 134.5-136° C.

Example 13

2-butyl-4-chloro-1-[2'-(1H-tetrazol-5-yl)1,1'-biphenyl-methyl]imidazole-5-carboxylic acid, 1-[(ethoxycarbonyl)oxy]methyl ester (compound 9)

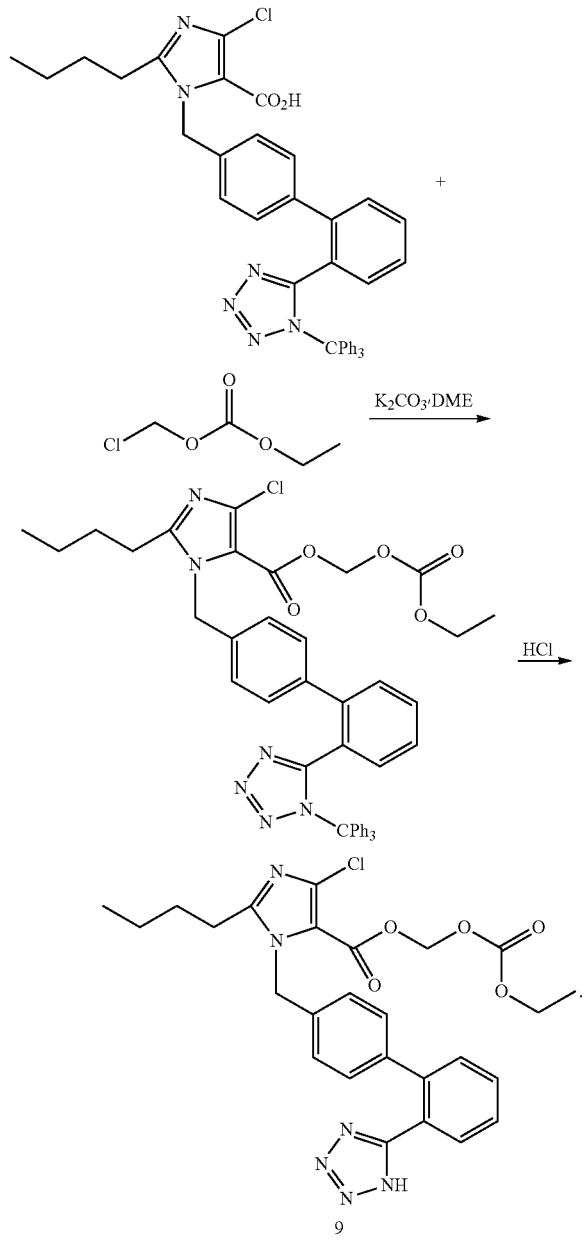

9

To a 100 ml of one-necked flask, 0.698 g of material, 0.162 g of potassium carbonate, 5 ml of N,N-dimethylacetamide were added in turn. The solution was stirred at room temperature for 20 minutes. Then 0.702 g of chloromethyl ethyl carbonate was added and the mixture was reacted at 45-50° C. for 16 hours. After the reaction was completed, the mixture solution was filtered, and 30 ml of water was added into the filtrate. The resulting mixture was extracted with 30 ml of ethyl acetate twice. The organic phase was dried and concentrated to give 1.854 g of oil, which was directly used in the next reaction without purification.

10 ml of dioxane and 5 ml of 4 mol/L HCl were added and the resulting mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.420 g of 2-butyl-4-chloro-1-[2'-(1H-tetrazol-5-yl)1,1'-biphenyl-methyl]imidazole-5-carboxylic acid, 1-[(ethoxycarbonyl)oxy]methyl ester.

$^1$H-NMR ($CDCl_3$) δ H (ppm) 0.92 (t, 3H, J=17.5), 1.23 (t, 3H, J=14.0), 1.37 (m, 2H, J=34.2), 1.73 (m, 2H, J=30.8), 2.69 (t, 2H, J=15.5), 4.13 (q, 2H, J=15.7), 5.58 (s, 2H), 5.89 (s, 2H), 6.99-7.61 (8H), 8.16 (d, 1H, J=6.1)

ESI (−): 539.1

Mp: 164.5-160° C.

Example 14

2-butyl-4-chloro-1-[2'-(1H-tetrazol-5-yl)1,1'-biphenyl-methyl]imidazole-5-carboxylic acid, 1-[(tert-butoxycarbonyl)oxy]methyl ester (compound 10)

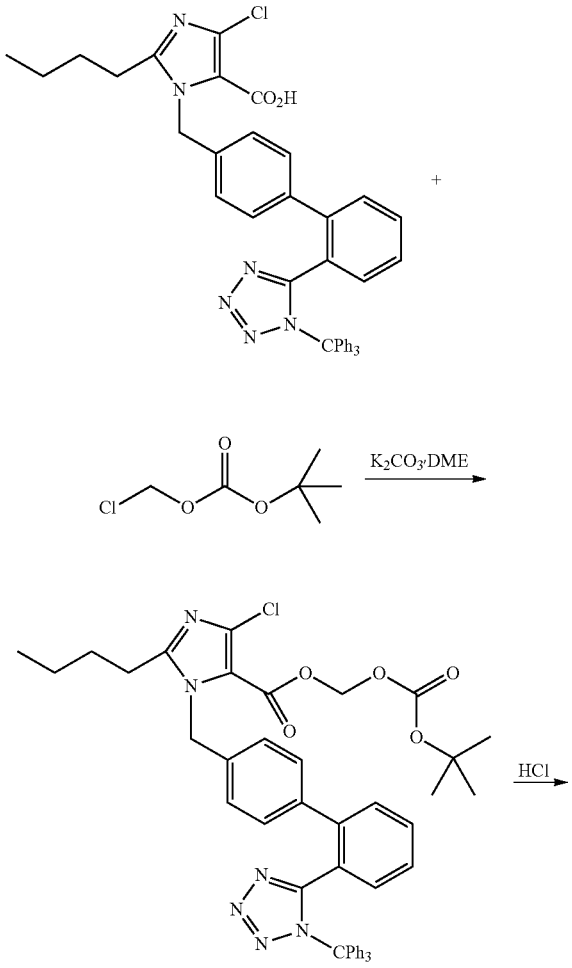

-continued

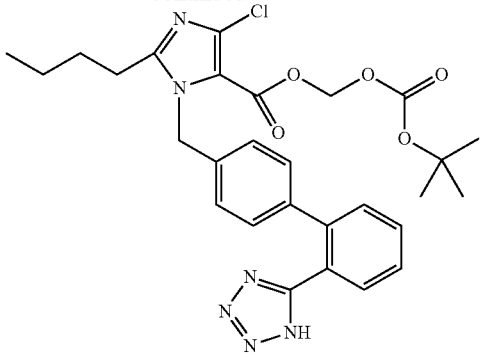

10

To a 100 ml of one-necked flask, 0.629 g of material 0.141 g of potassium carbonate, 5 ml of N,N-dimethylacetamide were added in turn. The solution was stirred at room temperature for 20 minutes. Then 0.625 g of chloromethyl tert-butyl carbonate was added and the mixture was reacted at 45-50° C. for 16 hours. After the reaction was completed, the mixture solution was filtered, and 30 ml of water was added into the filtrate. The resulting mixture was extracted with 30 ml of ethyl acetate twice. The organic phase was dried and concentrated to give 1.732 g of oil, which was directly used in the next reaction without purification.

10 ml of dioxane and 5 ml of 4 mol/L HCl were added and the resulting mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.349 g of 2-butyl-4-chloro-1-[2'-(1H-tetrazol-5-yl)1,1'-biphenyl-methyl]imidazole-5-carboxylic acid, 1-[(tert-butoxycarbonyl)oxy]methyl ester.

$^1$H-NMR ($CDCl_3$) δ H (ppm): 0.92 (t, 3H, J=17.1), 1.25 (s, 9H), 1.37 (m, 2H, J=32.0), 1.74 (m, 2H, J=29.3), 2.69 (t, 2H, J=14.9), 4.13 (q, 2H, J=15.5), 5.58 (s, 2H), 5.88 (s, 2H), 6.95-7.60 (8H), 8.17 (d, 1H, J=6.20)

ESI (−): 565.5

Test Example 1

Effect of Lowering Blood Pressure

A female spontaneously hypertensive rat (SHR) is anaesthetize by abdominal cavity injection with diazepam of 5 mg/kg and ketamine hydrochloride of 50 mg/kg and its back is fixed. An artery conduit is inserted from the left of a femoral artery to a lower abdominal aorta, and than a stomach fistula treatment is operated. After 20-30 hours for postoperative recovery, the artery conduit is connected to it pressure transducer by a perfusion three-way tube. Blood pressure signals per pulse are transformed into biologic signals by pressure transducer, and systolic blood pressures and diastolic blood pressures per pulse are real-time recorded by a computer. When the SHR is connected to the computer system for 4-5 hours, blood pressures and palpitation intervals in one hour are recorded as normal comparing data before administration. Afterwards, it is adminstrated with a dosage of 30 mg/kg and a volume of 2 ml/kg through the stomach fistula. Blood pressures in 6 hours after administration are continuously recorded to observe changes of systolic blood pressure and diastolic blood pressure.

Evaluation results of animal pharmacodynamics of the compounds of examples according to the present invention are in the following table:

| compounds | Before administration (mmHg) | Post-administration (mmHg) |
|---|---|---|
| Compound 1 | 166/112 | 159/103 |
| Compound 2 | 167/123 | 155/105 |
| Compound 3 | 168/114 | 158/102 |
| Compound 4 | 166/110 | 159/102 |
| Compound 5 | 166/112 | 157/101 |
| Compound 6 | 169/117 | 159/103 |
| Compound 7 | 168/115 | 157/103 |
| Compound 8 | 167/114 | 156/101 |
| Compound 9 | 170/118 | 159/104 |
| Compound 10 | 168/113 | 158/103 |

Test Example 2

An Efficiency of Active Metabolism Conversion

The SD rats are orally administrated by intragastric infusion with a dosage of 20 mg/kg. Blood samples are collected from an orbit at the time of 3 hours since the administration. The blood samples freely drop into centrifuge tubes. The sampling amount of blood is 0.3~0.5 ml, and the blood plasma is centrifugalized. After the sample is pre-treated, the blood is analyzed by using HPLC method to get the amount of EXP3174 in the blood plasma. Based on the molar ratio of the amount of EXP3174 and the amount of administration dosage, a ratio of the experiment compounds being converted into active metabolite in vivo may be calculated.

The result is as follows:

| compound | metabolism conversion ratio |
|---|---|
| HN-65021 | 1.5% |
| Compound 8 | 4.47% |
| Compound 9 | 4.64% |

Test Example 3

Evaluation of Toxicity

20 Kunming mice with weight of 18-22 g are randomly divided into two groups, each group including 10 ones with two identical halves for male and female. The mice are fasted for 6 hours, and then the two groups of mice are administrated by intragastric infusion with the compounds of the present invention in the amount of 10 g/kg, 5 g/kg, 2 g/kg. The administration volume is 0.8 ml/20 g, and the solvent is 0.5% CMC-Na. Observe and accumulate the number of dead animals during 14 days after administration (one administration) to calculate LD50. The compared data is as follows:

| compound | LD50 |
|---|---|
| losartan potassium | 2 g/kg |
| HN-65021 | 5-8 g/kg |
| Compound 8 | >10 g/kg |
| Compound 9 | >10 g/kg |
| Compound 10 | >10 g/kg |

Compared with the conventional Ang II receptor antagonists, the compounds of the invention have low toxicity and high efficiency of conversion with an equal effect of lowering blood pressure.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of formula (I), or its pharmaceutically acceptable salts, (I)

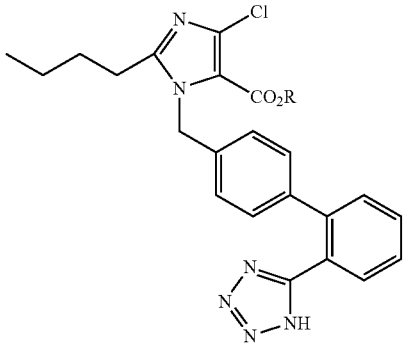

wherein R is

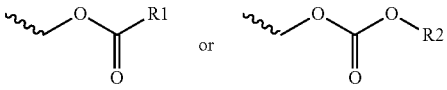

wherein R1 and R2 are independently selected from the group consisting of hydrogen, straight or branched $C_1$-$C_4$alkyl, and $C_3$-$C_7$cycloalkyl, and wherein the alkyl or the cycloalkyl group is unsubstituted or substituted by 1-3 substituents selected from the group consisting of F, Cl, Br, $NH_2$, and OH.

2. The compound [and] *or* its pharmaceutically acceptable salts according to claim 1, wherein R is

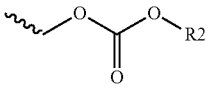

wherein R2 is selected from the group consisting of straight or branched $C_1$-$C_4$ alkyl, and $C_3$-$C_7$ cycloalkyl.

3. The compound [and] *or* its pharmaceutically acceptable salts according to claim 1 wherein R is

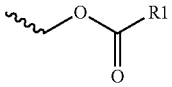

wherein R1 is selected from the group consisting of hydrogen, straight or branched $C_1$-$C_4$ alkyl, and $C_3$-$C_7$ cycloalkyl.

4. The compound [and] *or* its pharmaceutically acceptable salts according to claim 1 wherein R is

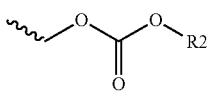

wherein R2 is selected from the group consisting of hydrogen, straight or branched $C_1$-$C_4$ alkyl, and $C_3$-$C_7$ cycloalkyl.

5. The compound [and] *or* its pharmaceutically acceptable salts according to claim 4, wherein R2 is straight or branched $C_1$-$C_4$ alkyl.

6. The compound or its pharmaceutically acceptable salts according to claim 1, wherein the compounds are selected from the following group consisting of:

2-butyl-4-chloro-1-[2'-(1H-tetrazol-5-yl)1,1'-biphenyl-methyl]imidazole-5-carboxylic acid, pivaloyloxymethyl ester;

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester;

2-butyl-4-chloro-1-[2'-(1H-tetrazol-5-yl)1,1'-biphenyl-methyl]imidazole-5-carboxylic acid, 1-[(ethoxycarbonyl)oxy]methyl ester; and 2-butyl-4-chloro-1-[2'-(1H-tetrazol-5-yl)1,1'-biphenyl-methyl]imidazole-5-carboxylic acid, 1-[(tert-butoxycarbonyl)oxy]methyl ester.

7. A pharmaceutical composition comprising 0.05-50 mg of the compound or its pharmaceutically acceptable salts according to claim 1, and pharmaceutically acceptable carriers, excipients or diluents.

8. A method of treating hypertension, by inhibiting I receptors of angiotensin II, comprising the step of administrating a patient in need of such treatment with the compound or its pharmaceutically acceptable salts according to claim 1 in the amount of 0.05-30 mg/kg weight/day.

9. A process to prepare the compound of formula I according to claim 1 *or a pharmaceutically acceptable salt thereof*, comprising the steps of:

(a) losartan potassium is oxidized to 2-butyl-4-chloro-1-[2'-(1H-tetrazol-5-yl)1,1'-biphenyl-methyl]imidazole-5-carboxylic acid;

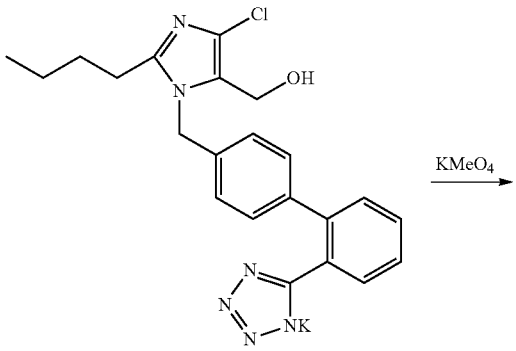

-continued

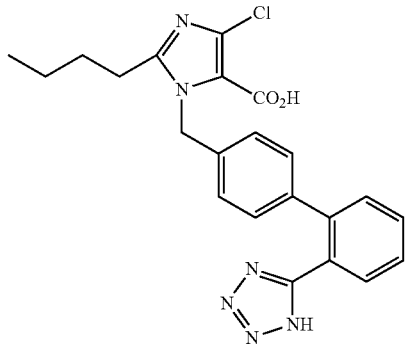

(b) the oxidative product obtained from step (a) is reacted with triphenylchloromethane to give 2-butyl-4-chloro-1-[2'-(1-triphenylmethyl-tetrazol-5-yl)1,1'-biphenyl-methyl]imidazole-5-carboxylic acid;

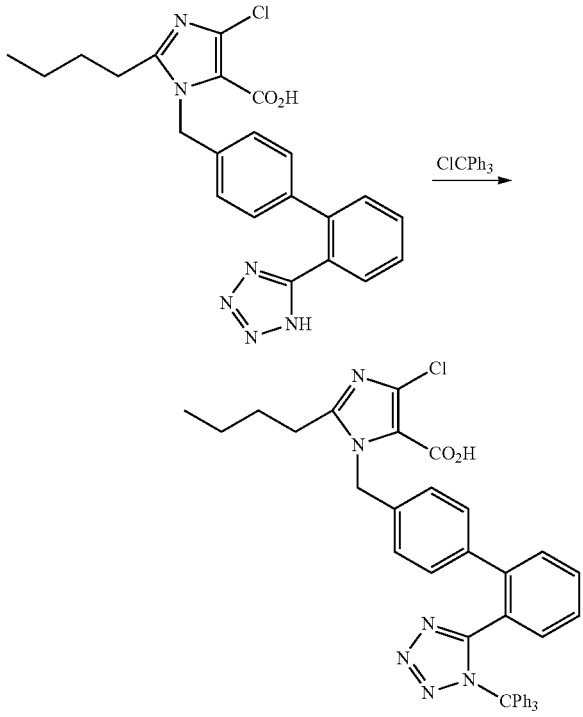

(c) the product obtained from the step (b) is reacted with the compounds of formula X—R to give esterified intermediates under alkaline condition; then the trityl is deprotected to give the compound of formula I, wherein X is halogen and R represents the following structures:

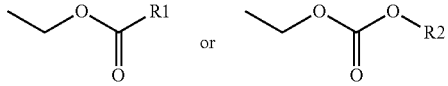

wherein, R1 and R2 are independently selected from the group consisting of hydrogen, straight or branched $C_1$-$C_4$ alkyl, and $C_3$-$C_7$ cycloalkyl,

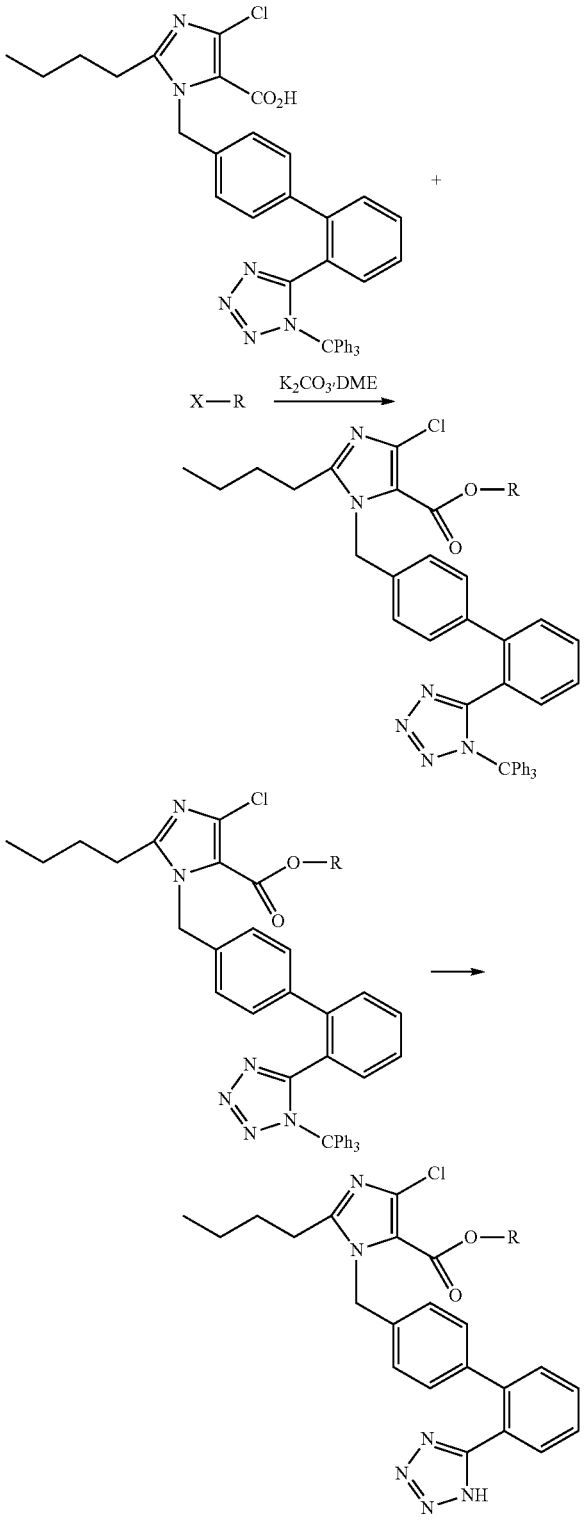

(*d*) *and optionally converting the product of step* (*c*) *to a pharmaceutically acceptable salt thereof.*

*10. A compound selected from:*

*2-butyl-4-chloro-1-[2'-(1H-tetrazol-5-yl)1,1'-biphenyl-methyl]imidazole-5-carboxylic acid, pivaloyloxymethyl ester;*

*2-butyl-4-chloro-1-[2'-(1H-tetrazol-5-yl)1,1'-biphenyl-methyl]imidazole-5-carboxylic acid, 1-[(isopropoxy-carbonyl)oxy]methyl ester;*

*2-butyl-4-chloro-1-[2'-(1H-tetrazol-5-yl)1,1'-biphenyl-methyl]imidazole-5-carboxylic acid, 1-[(ethoxycarbo-nyl)oxy]methyl ester; and*

*2-butyl-4-chloro-1-[2'-(1H-tetrazol-5-yl)1,1'-biphenyl-methyl]imidazole-5-carboxylic acid, 1-[(tert-butoxy-carbonyl)oxy]methyl ester.*

*11. 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester of the formula:*

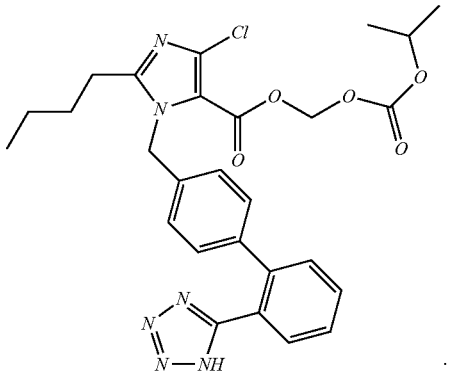

*12. A pharmaceutically acceptable salt of a compound selected from:*

*2-butyl-4-chloro-1-[2'-(1H-tetrazol-5-yl)1,1'-biphenyl-methyl]imidazole-5-carboxylic acid, pivaloyloxymethyl ester;*

*2-butyl-4-chloro-1-[2'-(1H-tetrazol-5-yl)1,1'-biphenyl-methyl]imidazole-5-carboxylic acid, 1-[(isopropoxy-carbonyl)oxy]methyl ester;*

*2-butyl-4-chloro-1-[2'-(1H-tetrazol-5-yl)1,1'-biphenyl-methyl]imidazole-5-carboxylic acid, 1-[(ethoxycarbo-nyl)oxy]methyl ester; and*

*2-butyl-4-chloro-1-[2'-(1H-tetrazol-5-yl)1,1'-biphenyl-methyl]imidazole-5-carboxylic acid, 1-[(tert-butoxy-carbonyl)oxy]methyl ester.*

*13. A pharmaceutically acceptable salt of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester.*

*14. A pharmaceutical composition comprising 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, and a pharmaceutically acceptable carrier, excipient, or diluent.*

*15. A pharmaceutical composition comprising a pharmaceutically acceptable salt of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, and a pharmaceutically acceptable carrier, excipient, or diluent.*

*16. A method of treating hypertension, by inhibiting the type I receptor of angiotensin II, comprising administrating to a patient in need of said treating an amount effective for treating hypertension of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester.*

*17. A method of treating hypertension, by inhibiting the type I receptor of angiotensin II, comprising administrating to a patient in need of said treating an amount effective for*

*treating hypertension of a pharmaceutically acceptable salt of 2-butyl-4-chloro-1-[2'-(1H-tetrazol-5-yl)1,1'-biphenyl-methyl]imidazole-5-carboxylic acid, 1-[(isopropoxycarbo-nyl)oxy]methyl ester.*

* * * * *